United States Patent [19]

Haaker et al.

[11] Patent Number: 5,117,446
[45] Date of Patent: May 26, 1992

[54] X-RAY DIAGNOSTIC APPARATUS COMPRISING MEANS FOR THE ENLARGED VISUAL DISPLAY OF A SELECTABLE DETAIL OF THE OVERALL IMAGE

[75] Inventors: Paul R. Haaker, Hamburg; Erhard P. A. Klotz, Halstenbek; Reiner H. Koppe, Hamburg; Rolf E. Linde, Haseldorf, all of Fed. Rep. of Germany

[73] Assignee: U. S. Philips Corporation, New York, N.Y.

[21] Appl. No.: 656,895

[22] Filed: Feb. 15, 1991

[30] Foreign Application Priority Data

Feb. 17, 1990 [DE] Fed. Rep. of Germany ....... 4005111

[51] Int. Cl.⁵ .............................................. H05G 1/64
[52] U.S. Cl. ........................................ 378/99; 378/62; 378/95; 358/111
[58] Field of Search ............... 378/99, 98, 62, 95, 378/145-147, 152; 358/111, 213.11, 213.13, 213.23

[56] References Cited

U.S. PATENT DOCUMENTS

| 4,442,538 | 4/1984 | Haendle | 378/99 |
| 4,606,064 | 8/1986 | Haendle | 378/99 |
| 4,749,257 | 6/1988 | Klausz | 378/99 |

OTHER PUBLICATIONS

Radiol. Diagn. 25 (1984), pp. 799-803.

Primary Examiner—Janice A. Howell
Assistant Examiner—David P. Porta
Attorney, Agent, or Firm—William Squire

[57] ABSTRACT

An X-ray diagnostic apparatus, comprises an X-ray source (1), an imaging surface (6) on which the intensity distribution of the X-rays to be applied to a test object (4) is imaged, an optical imaging device for imaging an overall image (10) of the imaging surface (6) onto the entrance surface of a first image sensor (11), a device (12) for the visual display of the overall image (10), and an imaging enlargement device for the enlarged visual display of a selectable detail of the overall image. Strongly enlarged and still high-resolution detail images are generated in that the selectable detail (20) of the overall image is directed onto a second image sensor 16) which discriminates a substantially higher number of pixels relative to the unit of surface area of the overall image.

11 Claims, 1 Drawing Sheet

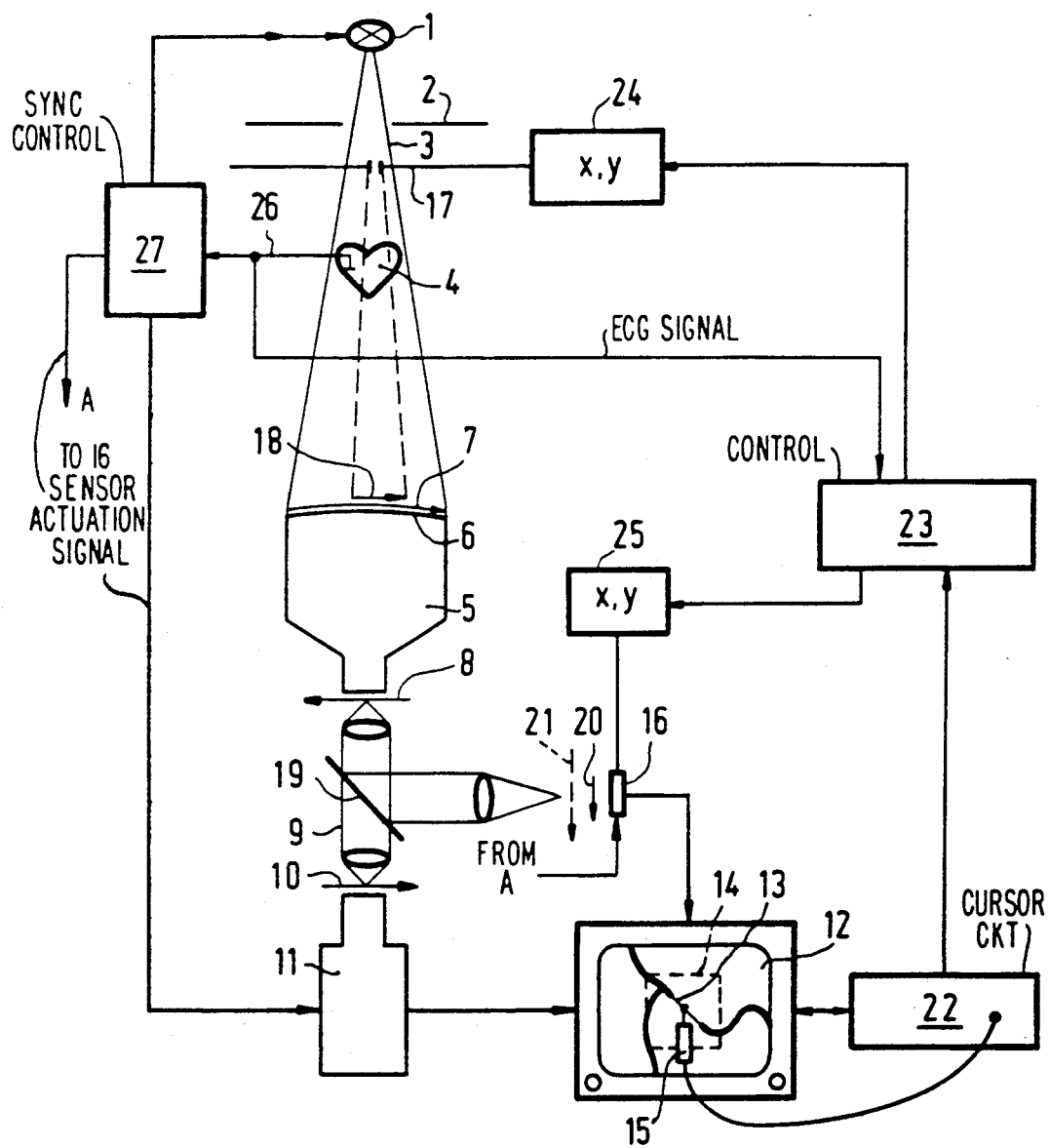

X-RAY DIAGNOSTIC APPARATUS COMPRISING MEANS FOR THE ENLARGED VISUAL DISPLAY OF A SELECTABLE DETAIL OF THE OVERALL IMAGE

The invention relates to an X-ray diagnostic apparatus, comprising an X-ray source, an imaging surface for forming an image of the intensity distribution of X-rays to be directed through a test object, an optical imaging device for imaging an overall image present on the imaging surface onto the entrance surface of a first image sensor, a device for visual display of the overall image, and means for the enlarged visual display of a selectable detail of the overall image.

In a device of this kind which is known from DE-OS 33 19 309 which corresponds to U.S. Pat. No. 4,606,064, there is provided a television pick up system whereby, using electronic means, a selectable image detail can be displayed on a monitor. The scanning speed, the horizontal frequency and the vertical frequency are modified therein so that an image detail is scanned with an increased number of pixels per unit of surface area. The number of pixels per unit of surface area can be increased only within given limits in an image pick up tube (Vidicon, Plumbicon), so that as the detail is enlarged further, an increasing lack of definition of the image detail is unavoidable.

It is an object of the invention to construct an X-ray diagnostic apparatus of the kind set forth so that high-resolution, substantially enlarged detail images can be simply generated.

This object is achieved in that the selectable detail of the overall image is directed onto a second image sensor which discriminates a substantially higher number of pixels with respect to the unit of surface area of the overall image.

For the observation of the overall image, adequate resolution is feasible, for example using a number of 512 × 512 pixels. When the same display surface area is to be filled as well as possible with an image having an enlarged detail, the second image sensor can be constructed in accordance with the invention, independently of the first sensor, so that the detail is displayed with at least substantially the same number of pixels and hence with the same definition.

For the first image sensor preferably a television camera comprising, for example a Vidicon or Plumbicon tube is chosen.

In order to ensure that the image detail can be quickly and simply detected by the second image sensor, in a further version of the invention a part of the radiation entering the optical imaging device is branched off so as to be directed onto the second image sensor.

Even though in principle arbitrary known image sensors can be used, for the second image sensor use is preferably made of a CCD image sensor which is capable of suitably detecting a large number of pixels on a small surface. CCD image sensors of this kind which are suitable for X-ray fluoroscopy are disclosed in Radiol. diagn. 25 (1984) pp. 799-803.

The branching off of a part of the radiation of the optical imaging device is not necessary when use is made of CCD sensors which directly detect X-rays and which can be inserted into the path of the X-rays behind the object to be tested. To this end, a luminescence detector (stimulatable phosphor) whose imaging surface is scanned by a laser beam is preferably used.

In a preferred version the entrance surface of the second image sensor is proportioned to be so small that only a detail of the overall image can be detected, the second image sensor being displaceable across the overall image in two coordinate directions. In that case image sensors are obtained which have a small surface area and which, because of their small volume and weight, can be readily displaced mechanically in two coordinate directions in the zone of the overall image which is to be examined in more detail.

In order to ensure that notably for medical applications the radiation dose for the patient is minimized, the X-ray source is succeeded by a diaphragm which transmits an X-ray field corresponding to the detail covered by the second image sensor. A further significant advantage of this solution consists in that the scattered radiation is thus minimized, so that the image contrast is enhanced and the radiation dose can be further reduced.

In order to simplify the adjusting procedure, the coordinate movements of the second image sensor and the diaphragm are controlled by a common control circuit.

A preferred solution in accordance with the invention is characterized in that the coordinate movements are controlled by a cursor circuit, the target being predetermined by a point-out pen aimed at the center of the detail to be enlarged of the visually displayed overall image. An X-ray diagnostic apparatus is thus obtained which can be readily operated and whereby substantially enlarged detail images can be produced of arbitrary locations on the basis of survey images observed by means of the first sensor.

For the imaging of periodically moving test objects, in a further version of the invention it is important that successive exposures are synchronised by the motion of the test object, for example a human heart.

Without necessitating substantial structural modifications of existing X-ray diagnostic apparatus, the invention enables a substantially more exact geometrical measurement of fine structures and is particularly suitable for medical applications. Better knowledge of the morphologic condition of vessels facilitates notably the intricate treatment of stenoses (constrictions of vessels).

IN THE DRAWINGS:

A preferred embodiment in accordance with the invention will be described in detail hereinafter with reference to the drawing.

The sole Figure shows the system lay out of an X-ray diagnostic apparatus in accordance with the invention which comprises a second image sensor.

DESCRIPTION OF THE PREFERRED EMBODIMENTS

The reference numeral 1 denotes an X-ray source which may be of a conventional design. The X-ray source emits an X-ray beam, constricted by a diaphragm 2, in the direction of an object to be examined, for example, a heart 4. The radiation irradiating the object to be examined forms a shadow image 7 on the imaging surface 6 of the X-ray image intensifier 5. The output of the X-ray image intensifier 5 delivers an intensified image 8 which is detected, via the optical imaging device 9, as an overall image 10 by the target of a TV camera 11 and which is visually displayed on the display screen 12. A stenosis 13 is visible which is to be observed more closely by enlarging the area 14 (denoted by a broken line) so far that is fills the entire surface of the display screen.

The operator indicates the position of the detail by means of a point-out pen 15 aimed at the center of the area 14. Subsequently, the second CCD image sensor 16 detects the desired detail image and converts it into a video signal enabling full-screen display on the display screen 12.

In order to reduce the radiation dose, notably for a patient, and also the contrast-reducing scattered radiation, there is provided a diaphragm 17 which transmits only an X-ray beam constricted to the image detail, so that only a correspondingly smaller shadow image 18 is formed on the imaging surface 6 of the X-ray image intensifier, which shadow image fills the entrance surface of the second CCD image sensor 16 as a detail image 20 via the semi-transparent mirror 19 of the optical imaging device 9. In the absence of the diaphragm 17, a substantially large overall image 21 would be available at this area, the overall image corresponding to the overall image 10.

Depending on the control signals received from the cursor circuit 22, the control circuit 23 initiates movements of the manipulators 24 and 25 in the coordinate directions x and y, so that the diaphragm 17 and the CCD image sensor 16 are respectively by the moved manipulator to the target position predetermined by the point-out pen 15.

In order to ensure that successive exposures, for example the overall exposure and the detail exposure, always takes place in the same phase position of the rythmic cardiac movement, there is provided a synchronisation control circuit 27 which is controlled by an ECG signal 26 and which each time ensures activation of the X-ray source 1 and the image sensors 11 and 16 in the same phase. Evidently, there may be provided memory circuits which store the detected image data of the sensors 11 and 16.

The overall image 10 is displayed on the display screen 12 with a number of pixels of, for example, 512×512. The detail image 20, to be enlarged, for example, 6 times, is detected by the CCD sensor 16 with a number of pixels amounting to 300×400. Because of its small dimensions of approximately 1.5×1 cm², this CCD sensor 16 requires only little structural effort for displacement by means of the manipulator. The same holds good for the manipulator 24.

The pixel density, relative to the unit of surface area of the overall image 10 or 20, is thus multiplied for the detail image 20 displayed on the display screen 12, so that structures of details of the stenosis 13 can be more exactly determined.

In the alternative, the sensor 20 can be a luminescence detector whose imaging surface is scanned by a laser beam.

We claim:

1. An X-ray diagnostic apparatus, comprising: an X-ray source, first imaging means for forming an image of the intensity distribution of X-rays directed through a test object, first and second image sensors, optical imaging means for imaging an overall image presented by the first imaging means onto the entrance surface of said first image sensor, display means for visual display of the overall image means for enlarging the visual display of a selectable detail of the overall image and means for directing at least a portion of the overall image onto said second imaging sensor which exhibits a substantially higher number of pixels with respect to the unit of surface area of the overall image than said first sensor.

2. An X-ray diagnostic apparatus as claimed in claim 1, wherein the first image sensor is a video camera.

3. An X-ray diagnostic apparatus as claimed in claim 1 wherein said optical imaging means branches a part of the radiation entering the optical imaging so as to be directed onto the second image sensor.

4. An X-ray diagnostic apparatus as claimed in claim 1 wherein the second image sensor is a CCD image sensor.

5. An X-ray diagnostic apparatus as claimed in claim 1 wherein the second imaging sensor is a CCD sensor which detects X-ray and includes means for inserting the second sensor into the path of the X-rays behind the object to be tested.

6. An X-ray diagnostic apparatus as claimed in claim 5, wherein the second image sensor is a luminescence detector whose imaging surface is scanned by a laser beam.

7. An X-ray diagnostic apparatus as claimed in claim 1 wherein the entrance surface of the second imaging sensor is proportioned to be so small that only a portion of the overall image is detected, and means for displacing the second imaging sensor across the overall image in two coordinate directions.

8. An X-ray diagnostic apparatus as claimed in claim 7, wherein the X-ray source is succeeded by a diaphragm which transmits an X-ray field corresponding to the portion sensed covered by the second image sensor.

9. An X-ray diagnostic apparatus as claimed in claim 7, wherein the coordinate movements of the second image sensor and the diaphragm are controlled by a common control circuit.

10. An X-ray diagnostic apparatus as claimed in claim 7 wherein the coordinate movements are controlled by a cursor circuit, the target being predetermined by a point-out pen aimed at the center of the portion for enlargement of that portion of the visually displayed overall image.

11. An X-ray diagnostic apparatus as claim in claim 1 wherein for examination of a periodically moving test object, said apparatus includes means for synchronizing the X-ray pulses with the motion of the test object.

* * * * *